United States Patent
Shimohata et al.

(10) Patent No.: US 10,930,696 B2
(45) Date of Patent: Feb. 23, 2021

(54) IMAGE PICKUP UNIT, ENDOSCOPE, AND METHOD FOR MANUFACTURING IMAGE PICKUP UNIT

(71) Applicant: OLYMPUS CORPORATION, Tokyo (JP)

(72) Inventors: Takahiro Shimohata, Shiojiri (JP); Takatoshi Igarashi, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/352,954

(22) Filed: Mar. 14, 2019

(65) Prior Publication Data

US 2019/0214426 A1    Jul. 11, 2019

Related U.S. Application Data

(63) Continuation of application No. PCT/JP2016/081896, filed on Oct. 27, 2016.

(51) Int. Cl.
*H01L 27/146* (2006.01)
*A61B 1/05* (2006.01)
(Continued)

(52) U.S. Cl.
CPC ...... *H01L 27/14636* (2013.01); *A61B 1/0011* (2013.01); *A61B 1/05* (2013.01);
(Continued)

(58) Field of Classification Search
None
See application file for complete search history.

(56) References Cited

U.S. PATENT DOCUMENTS

| 2004/0130640 A1 | 7/2004 | Fujimori |
| 2012/0170923 A1* | 7/2012 | Seo ...................... H04N 5/2253 |
| | | 396/133 |

(Continued)

FOREIGN PATENT DOCUMENTS

| EP | 1577950 A1 | 9/2005 |
| JP | H09-46566 A | 2/1997 |

(Continued)

OTHER PUBLICATIONS

International Search Report dated Dec. 27, 2016 issued in PCT/JP2016/081896.

*Primary Examiner* — Xiaoming Liu
(74) *Attorney, Agent, or Firm* — Scully, Scott, Murphy & Presser, P.C.

(57) ABSTRACT

An image pickup unit includes: an image pickup device; a device laminate in which a plurality of semiconductor devices are laminated; and a signal cable having a lead wire and a shield lead wire. The plurality of semiconductor devices have cutouts. A groove in parallel with an optical axis direction is configured on a side surface of the device laminate by a plurality of the cutouts which communicate with one another. On cutout surfaces of the semiconductor devices, side electrodes are arranged. The lead wire and the shield lead wire are housed in the respective cutouts which have diameters in accordance with respective diameters of the lead wire and the shield lead wire. The lead wire is bonded to the side electrode and the shield lead wire is bonded to the side electrode.

7 Claims, 9 Drawing Sheets

(51) Int. Cl.
*H01L 27/14* (2006.01)
*H04N 5/369* (2011.01)
*A61B 1/00* (2006.01)
*H04N 5/225* (2006.01)

(52) U.S. Cl.
CPC .............. *A61B 1/051* (2013.01); *H01L 27/14* (2013.01); *H01L 27/14618* (2013.01); *H01L 27/14632* (2013.01); *H01L 27/14687* (2013.01); *H04N 5/369* (2013.01); *H04N 2005/2255* (2013.01)

(56) References Cited

U.S. PATENT DOCUMENTS

2012/0206583 A1* 8/2012 Hoshi .................. H04N 5/2253
348/76
2016/0367122 A1* 12/2016 Ichimura ................ A61B 1/051

FOREIGN PATENT DOCUMENTS

| JP | 2004-134128 A | 4/2004 |
| JP | 2004-207461 A | 7/2004 |
| JP | 2004-304081 A | 10/2004 |
| JP | 2005-334509 A | 12/2005 |
| JP | 2011-097294 A | 5/2011 |
| JP | 2012-074672 A | 4/2012 |
| JP | 5032704 B2 | 9/2012 |
| JP | 5945653 B1 | 7/2016 |
| WO | WO 2004/059740 A1 | 7/2004 |
| WO | WO 2016/063603 A1 | 4/2016 |

* cited by examiner

IMAGE PICKUP UNIT, ENDOSCOPE, AND METHOD FOR MANUFACTURING IMAGE PICKUP UNIT

CROSS REFERENCE TO RELATED APPLICATION

This application is a continuation application of PCT/JP2016/081896 filed on Oct. 27, 2016, the entire contents of which are incorporated herein by this reference.

BACKGROUND OF THE INVENTION

1. Field of the Invention

The present invention relates to an image pickup unit which includes an image pickup device, a device laminate in which a plurality of semiconductor devices are laminated, and an electric member; an endoscope including the image pickup unit which includes the image pickup device, the device laminate, and the electric member; and a method for manufacturing the image pickup unit which includes the image pickup device, the device laminate, and the electric member.

2. Description of the Related Art

An endoscope obtains images of an inside of a patient or the like by inserting an insertion portion with an image pickup unit housed at a rigid distal end portion of the insertion portion, for example, into the inside of the patient. In Japanese Patent Application Laid-Open Publication No. 2005-334509, an image pickup unit including a wiring board on which an electronic component chip such as a capacitor configuring a driving circuit, a resistor, and an IC is mounted and which is bonded onto a rear surface of an image pickup device is disclosed.

In recent years, a semiconductor device on which a planar device (thin film component) having the same function as an electronic component chip such as a capacitor is formed has been developed. By bonding a device laminate including a plurality of laminated semiconductor devices, on each of which the planar device is formed, onto a rear surface of an image pickup device, an image pickup unit can be shortened.

SUMMARY OF THE INVENTION

An image pickup unit according to an embodiment of the present invention includes: an image pickup device including a light receiving surface and a rear surface facing the light receiving surface; a device laminate bonded to the rear surface of the image pickup device, the device laminate including a plurality of semiconductor devices laminated via sealing resin layers; and an electric member including an electrode part, a cutout is formed in an outer peripheral portion of the semiconductor device laminated on a rearmost side among the plurality of semiconductor devices, a side electrode is arranged on a cutout surface, the electric member is housed in the cutout, and the electrode part of the electric member is bonded to the side electrode.

An image pickup unit according to another embodiment includes: an image pickup device including a light receiving surface and a rear surface facing the light receiving surface; a device laminate bonded to the rear surface of the image pickup device, the device laminate including a plurality of semiconductor devices laminated via sealing resin layers; and an electric member including electrode parts, in which cutouts are formed respectively in outer peripheral portions of a plurality of semiconductor devices successively laminated and including a semiconductor device laminated on a rearmost side among the plurality of semiconductor devices, a groove in parallel with an optical axis direction is configured in a side surface of the device laminate by a plurality of the cutouts communicating with one another, a side electrode is arranged on at least one cutout surface of the semiconductor devices, the electric member is housed in the groove, and the electrode parts of the electric member are bonded to the side electrode.

An endoscope according to further another embodiment includes an image pickup unit. The image pickup unit includes: an image pickup device including a light receiving surface and a rear surface facing the light receiving surface; a device laminate bonded to the rear surface of the image pickup device, the device laminate including a plurality of semiconductor devices laminated via sealing resin layers; and an electric member including electrode parts, in which cutouts are formed in outer peripheral portions of a plurality of semiconductor devices successively laminated and including a semiconductor device laminated on a rearmost side among the plurality of semiconductor devices, a groove in parallel with an optical axis direction is configured in a side surface of the device laminate by a plurality of the cutouts communicating with one another, a side electrode is arranged on at least one cutout surface of the semiconductor devices, the electric member is housed in the groove, and the electrode parts of the electric member are bonded to the side electrode.

A method for manufacturing an image pickup unit according to still another embodiment includes: fabricating an image pickup wafer which has a light receiving surface and a rear surface facing the light receiving surface and includes a plurality of image pickup devices; fabricating a first device wafer which includes a plurality of first semiconductor devices and a second device wafer which includes a plurality of second semiconductor devices; forming a plurality of first through-holes in predetermined arrangement in the first device wafer and forming a plurality of second through-holes in the predetermined arrangement in the second device wafer; arranging a first electrode film on a wall surface of each of the plurality of first through-holes of the first device wafer and arranging a second electrode film on a wall surface of each of the plurality of second through-holes of the second device wafer; fabricating a laminated wafer by laminating the image pickup wafer, the first device wafer, and the second device wafer via sealing resin layers so as to superimpose the first through-holes and the second through-holes; cutting the laminated wafer along cutting lines passing through centers of the first through-holes and fabricating a device laminate having a groove on a side surface of the device laminate, each of the first electrode film and the second electrode film arranged on an internal surface of the groove; and housing an electric member having a size in accordance with a size of the groove in the groove and bonding two electrodes of the electric member to the first electrode film or the second electrode film.

DETAILED DESCRIPTION OF THE PREFERRED EMBODIMENT(S)

First Embodiment

As shown in FIG. 1 to FIG. 4D, an image pickup unit 1 according to the present embodiment includes an image pickup device 10, a device laminate 20, and a signal cable 30 which is an electric member.

Note that in the following description, the drawings based on each embodiment are schematic, and respective relationships between thicknesses and widths of respective parts, ratios of the thicknesses and relative angles of the respective parts, and the like are different from those in reality. Further, in the respective drawings, portions having relationships and ratios of dimensions which are different from one another may be included. In addition, illustration of part of the components, for example, sealing resin layers, may be omitted in the drawings.

In addition, of optical axis directions, a direction in which the image pickup device 10 is located (Z-axis value increasing direction) is referred to as a front side. A direction in which the device laminate 20 is located (Z-axis value decreasing direction) is referred to as a rear side. In addition, of directions orthogonal to the optical axis, a Y-axis direction is referred to as an upper direction/lower direction, and an X-axis direction is referred to as a left direction/right direction. A dimension in the front and rear direction is referred to as a "length", a dimension in the right and left direction is referred to as a "width", and a dimension in the upper and lower direction is referred to as a "height (depth)".

The image pickup device 10 which is rectangular in a plan view, that is, which is rectangular in a sectional view in a direction orthogonal to an optical axis O (Z-axis) is a substantially rectangular parallelepiped flat plate which includes: a light receiving surface 10SA on which a light receiving part 11 is formed; a rear surface 10SB facing the light receiving surface 10SA; and four side surfaces. On the light receiving surface 10SA of the image pickup device 10, a cover glass 15 is bonded via a transparent bonding layer 19.

As described later, the cover glass 15, the image pickup device 10, and the device laminate 20 constitute an image pickup laminate 40 in a substantially rectangular parallelepiped shape, which is fabricated by cutting a laminated wafer 40W (see FIG. 7).

The light receiving part 11 is a CCD or a CMOS light receiving element or the like and generates an electric signal by receiving light and performing photoelectric conversion. The light receiving part 11 is connected to an electrode of the rear surface 10SB via through-wiring, although the connection is not shown.

The device laminate 20 includes four semiconductor devices 21 to 24 which are respectively laminated via sealing resin layers (underfill) 29. The sealing resin layers 29 are formed of an insulating resin such as an epoxy resin, an acrylic resin, a polyimide resin, a silicone resin, or a polyvinyl resin.

The device laminate 20 processes an electric signal outputted by the image pickup device 10 and outputs the processed signal as an image pickup signal. On each of the semiconductor devices 21 to 24, a planar device 28 which constitutes an electronic component functional circuit such as a capacitor, a resistor, or a buffer or a signal processing circuit such as a noise removal circuit or an analog-digital converter circuit is formed.

A thickness of each of the plurality of semiconductor devices 21 to 24 is approximately 30 μm to 100 μm, and thicknesses of the plurality of semiconductor devices 21 to 24 may be different from one another as described later. In addition, the planar device 28 may be formed on one surface of each of the semiconductor devices 21 to 24, and the planar devices 28 may be formed on both surfaces of each of the semiconductor devices 21 to 24. In addition, it is only required for the number of laminated semiconductor devices of the device laminate 20 to be equal to or greater than two, and the number of laminated semiconductor devices is not limited to four as in the present example.

The semiconductor devices 21 to 24 are connected to one another via through-wiring (not shown) and bumps 27 (see FIG. 4A and the like), each of which has a height of 5 μm to 50 μm. A front end surface of the device laminate 20 is connected to an electrode of the rear surface 10SB of the image pickup device 10 via the bumps 27. Also between the rear surface 10SB of the image pickup device 10 and the front end surface of the device laminate 20, a sealing resin layer 29A (29) is arranged. Resins forming the sealing resin layer 29 and the sealing resin layer 29A may be different from each other.

In respective outer peripheral portions of the plurality of semiconductor devices 21 to 24, cutouts T21 to T24, each of which is of a substantially semicircular shape in a sectional view in the direction orthogonal to the optical axis, are formed. In a side surface of the device laminate 20, the plurality of cutouts T21 to T24 communicating with one another constitute a groove T20 in parallel with the optical axis direction.

On cutout surfaces of the semiconductor devices 21 and 23, side electrodes 21C and 23C, each of which is formed of a conductive material such as copper and has a film thickness of 1 μm to 5 μm, are arranged. Each of the side electrodes 21C and 23C is connected to the bumps 27 or the planar device 28.

A lower half of a distal end portion (bonding portion) of the signal cable 30 is housed in the groove T20. The signal cable 30 is a shielded cable and includes a lead wire (core wire) 31, a lead wire covering layer 32 covering the lead wire 31, a shield lead wire 33 covering the lead wire covering layer 32, and an external covering layer 34 covering the shield lead wire 33 as a plurality of constituent members in sizes (external diameters) differing from one another. The lead wire 31 and the shield lead wire 33 can be deemed as electrode parts of the signal cable 30 which is the electric member.

As shown in FIG. 4A to FIG. 4D, the lead wire 31 having an external diameter R31 is housed in the cutout T21 which is of a substantially semicircular shape (with a diameter R21) in the sectional view. The lead wire covering layer 32 having a diameter R32 is housed in the cutout T22 having a diameter R22. The shield lead wire 33 having a diameter R33 is housed in the cutout T23 having a diameter R23. The external covering layer 34 having a diameter R34 is housed in the cutout T24 having a diameter R24.

The diameters of the signal cable 30 are in relationship of (R31<R32<R33<R34). The diameters of a plurality of cutouts T21 to T24, each of which is of the substantially semicircular shape, are in relationship of (R21<R22<R23<R24). The plurality of cutouts T21 to T24 having the diameters R in the sectional view which are different from one another, each of which is of a substantially semicircular shape, communicate with one another and thus, constitute the groove T20 of the device laminate 20. In other words, a size of the groove T20 becomes maximized on a rear end surface and is gradually decreased toward a front portion of the groove T20 in a step-wise manner.

The lead wire 31 is bonded to a side electrode 21C in the cutout T21 of the semiconductor device 21 on a front side (leading end side: position closest to the image pickup device 10) and the shield lead wire 33 is bonded to a side electrode 23C in the cutout T23 of the semiconductor device 23 on a rear side (proximal end side), respectively via, for example, a conductive paste.

The diameters of the cutouts T21 to T24 (R21 to R24) are set in accordance with the respective diameters (R31 to R34) so as to allow the lead wire 31, the lead wire covering layer 32, the shield lead wire 33, and the external covering layer 34, which are the plurality of constituent members constituting the signal cable 30, to be housed in the cutouts T21 to T24.

In other words, the plurality of constituent members of the signal cable 30 which is the electric member are housed in grooves (cutouts) in sizes according to the sizes of the respective constituent members.

For example, the diameter R21 of the cutout T21 in which the side electrode 21C is formed and the diameter R31 of the lead wire 31 are in relationship of (R21≥R31) and preferably, are in relationship of (1.01×R31<R21<1.20×R31). A size of the cutout T23 in which the side electrode 23C is formed and a size of the shield lead wire 33 are in the similar relationship. Since with the diameters of the cutouts and the diameter of the constituent members being in the above-described relationship, a substantially fitting state is achieved, arrangement and bonding in predetermined positions are facilitated.

Note that strictly speaking, the diameter (external dimension) of the cutout in which the side electrode is formed is a dimension of a surface of the side electrode which is of the semicircular shape in the sectional view. For example, when a diameter R21 of the cutout T21, which is of the semicircular shape and in which the side electrode 21C having a film thickness of 1 μm is formed in an internal surface (cutout surface), is described to be 50 μm, a diameter R21 of the cutout formed in the semiconductor device 21 (of a circular through-hole H21 formed in a device wafer 21W shown in FIG. 6) is 52 μm.

On the other hand, the diameter R22 of the cutout T22 in which no side electrode is formed and the diameter R32 of the lead wire covering layer 32 are in relationship of (R22≥R32) and preferably, are in relationship of (1.01×R32<R22<1.50×R32). When the size of the cutout in which no side electrode is formed is sufficiently larger than a size of an electronic component, as described later, upon fabricating the laminated wafer, it does not occur that an excessive sealing resin covers the side electrodes.

In addition, a length of each of the lead wire 31, the lead wire covering layer 32, and the shield lead wire 33 is set to be substantially the same as a thickness of each of the semiconductor devices 21 to 23 (and of the sealing resin layer 29).

In other words, the groove T20 of the device laminate 20 is constituted of the plurality of cutouts T21 to T24 having the sizes (diameters and lengths), which are different from one another, in accordance with the sizes (diameters and lengths) of the housed constituent members of the signal cable 30.

Since the image pickup unit 1 includes the device laminate 20, instead of a wiring board on which a chip electronic component is mounted, the image pickup unit 1 is short and small.

Further, in the image pickup unit 1, the signal cable 30 is housed in the groove T20 in the side surface of the device laminate 20, and the lead wire 31 and the shield lead wire 33 which are the electrode parts are bonded to the side electrodes 21C and 23C in the groove T20. Since in the image pickup unit 1, the portion where the signal cable 30 and the device laminate 20 are bonded is not located behind the device laminate 20, the image pickup unit 1 is particularly short and small.

In addition, an external dimension (a height or a width) of the device laminate 20, which is a wafer level laminate, in the direction orthogonal to the optical axis is the same as the size of the image pickup device 10 in the plan view. In other words, the device laminate 20 projected on a projection plane in the direction orthogonal to the optical axis is arranged within a projection plane of the image pickup device 10.

In the image pickup unit 1, the signal cable 30 is housed in the side surface of the device laminate 20. However, an approximately half of the diameter of the signal cable 30 is housed in the groove T20. Therefore, the external dimension (height) of the image pickup unit 1 in the direction orthogonal to the optical axis is a dimension of a small diameter which is calculated by adding the half of the diameter of the signal cable 30 to the height of the device laminate 20.

<A Method for Manufacturing an Image Pickup Unit 1>

Figure 1:
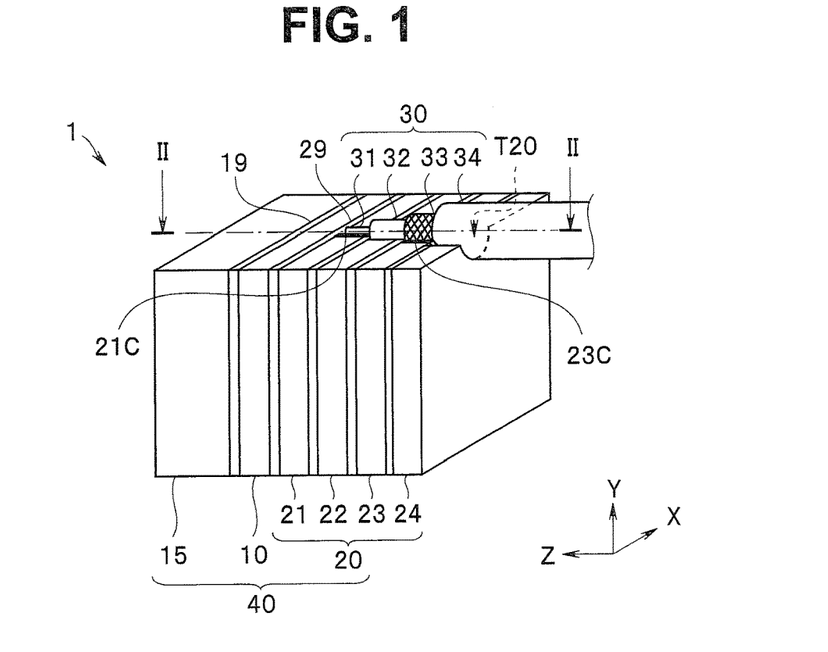
FIG. 1 is a perspective view of an image pickup unit according to a first embodiment.
Figure 2:
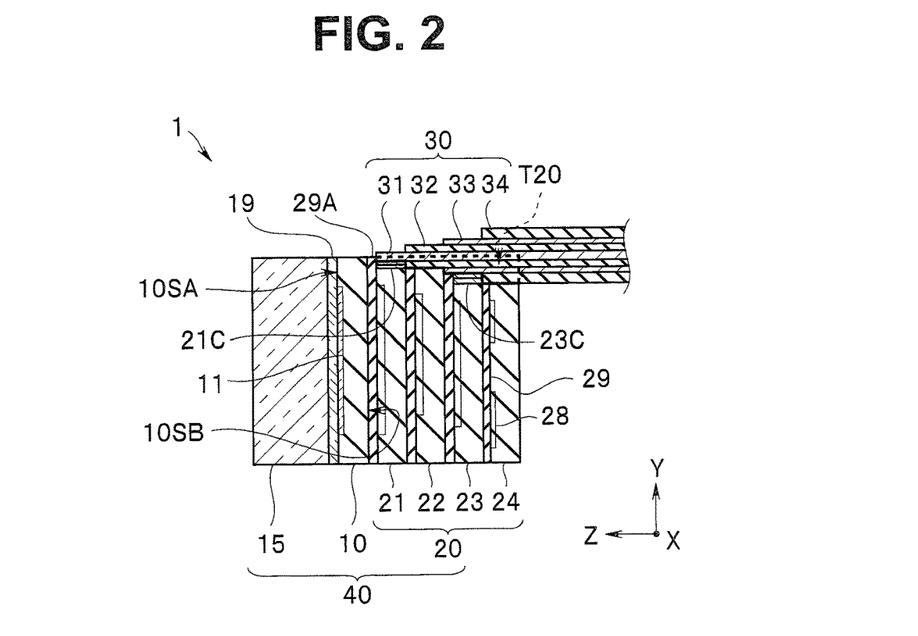
FIG. 2 is a sectional view of the image pickup unit according to the first embodiment, viewed along a line II-II in FIG. 1.
Figure 3:
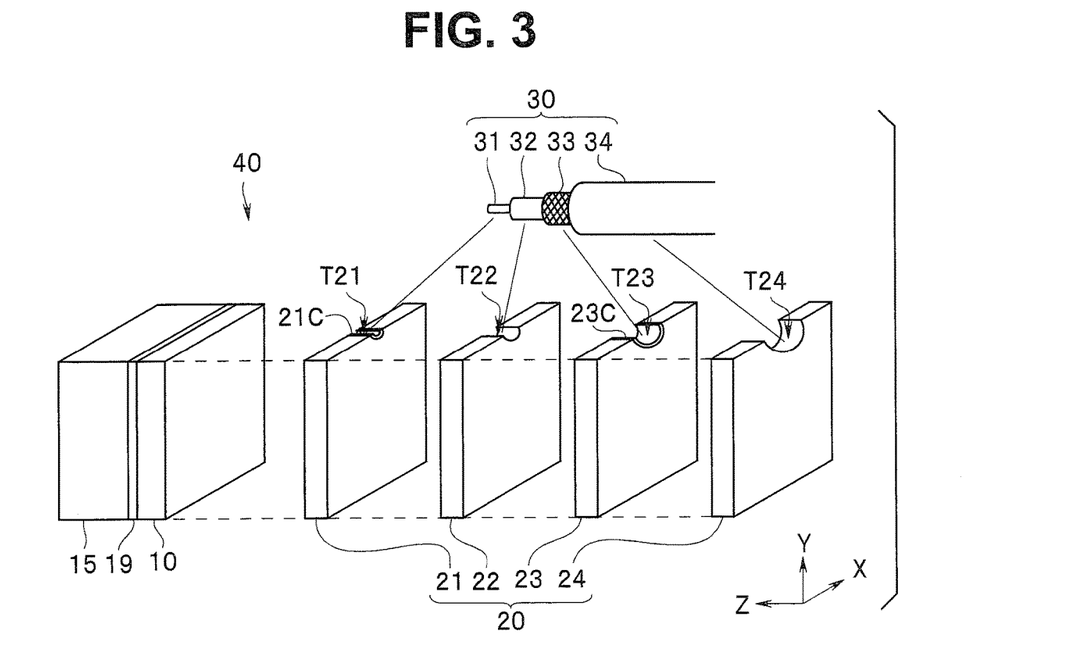
FIG. 3 is an exploded view of the image pickup unit according to the first embodiment.
Figure 4A:
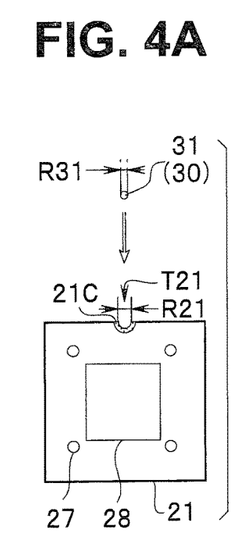
FIG. 4A is an exploded view of a semiconductor device and a signal cable according to the first embodiment.
Figure 4B:
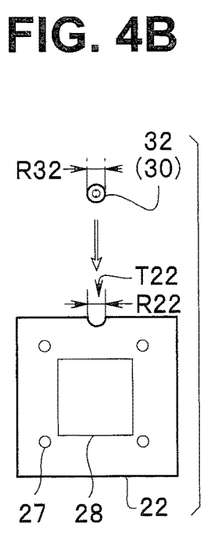
FIG. 4B is an exploded view of the semiconductor device and the signal cable according to the first embodiment.
Figure 4C:
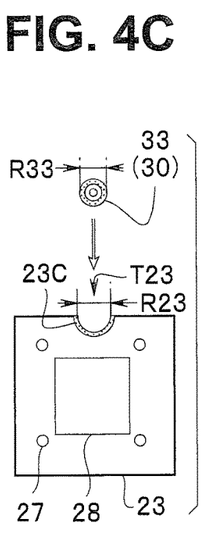
FIG. 4C is an exploded view of the semiconductor device and the signal cable according to the first embodiment.
Figure 4D:
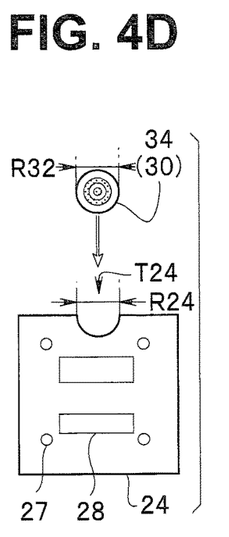
FIG. 4D is an exploded view of the semiconductor device and the signal cable according to the first embodiment.
Figure 5:
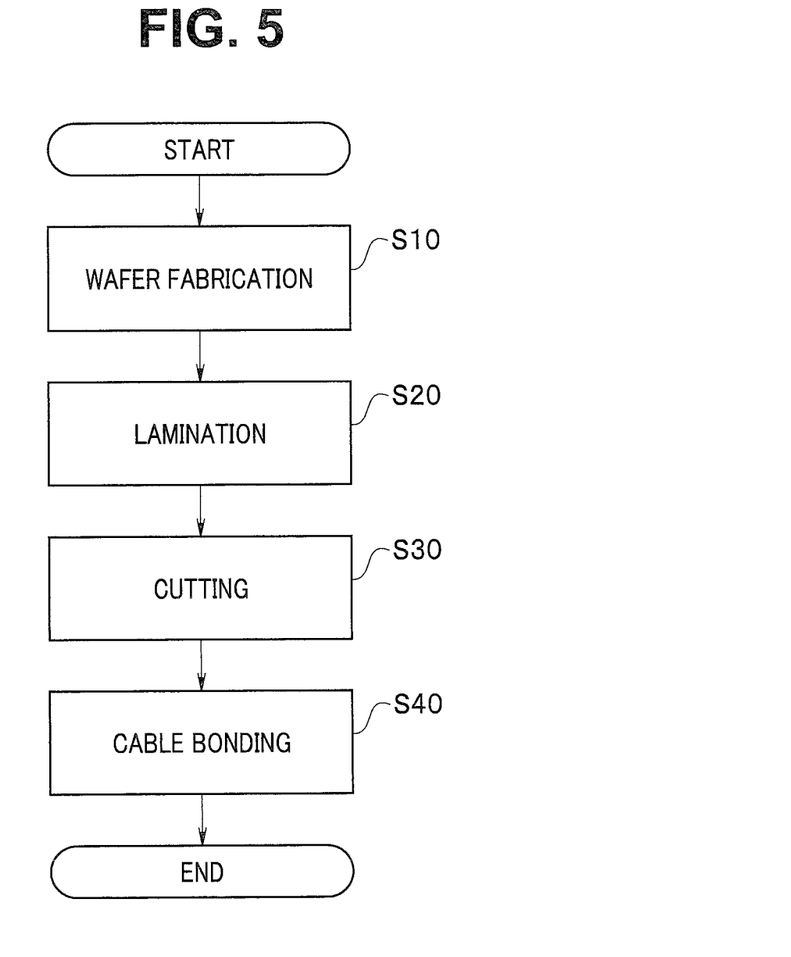
FIG. 5 is a flowchart of a method for manufacturing the image pickup unit according to the first embodiment.

Next, with reference to a flowchart shown in FIG. 5, a method for manufacturing an image pickup unit 1 will be described.

<Step S10> Wafer Fabrication Step

A wafer fabrication step includes an image pickup wafer fabrication step (S10A), a device wafer fabrication step (S10B) of fabricating a plurality of device wafers, a through-hole formation step (S10C) of forming through-holes in the device wafers, and an electrode film arrangement step (S10D) of arranging electrode films in the through-holes of the device wafers.

<S10A: Image Pickup Wafer Fabrication Step>

On a semiconductor wafer formed of silicon or the like, an image pickup wafer 10W (see FIG. 7) including a plurality of image pickup devices 10 is fabricated by employing the heretofore known semiconductor manufacturing technology. Each of the image pickup devices 10 includes a light receiving part 11 constituted of a CMOS image sensor or a CCD, a plurality of through-wires connected to the light receiving part 11, and the like. Before fabricating the through-wires and the like, a glass wafer 15W for protecting the light receiving part 11 is bonded to the image pickup wafer 10W.

<S10B: Device Wafer Fabrication Step>

On the semiconductor wafer formed of the silicon or the like, device wafers 21W to 24W (see FIG. 6 and FIG. 7) including a plurality of semiconductor devices 21 to 24 are fabricated by employing the heretofore known semiconductor manufacturing technology (for example, RIE). On each of the semiconductor devices 21 to 24, in accordance with use, a planar device 28 is formed. The semiconductor devices 21 to 24 have sizes which are the same as one another, and the plurality of semiconductor devices 21 to 24 are arranged in the device wafers 21W to 24W in the same arrangement.

<S10C: Through-Hole Formation Step>

In each of the device wafers 21W to 24W, a plurality of through-holes H21 to H24 are formed in the same predetermined arrangement. Note that each broken line shown in FIG. 6 indicates each cutting line CL at the later-described step S30. In other words, the arrangement of the plurality of through-holes H21 to H24 is set such that each cutting line CL passes through centers of the through-holes H21 to H24.

Diameters of the through-holes formed in the device wafers 21W to 24W are designed in accordance with respective diameters (sizes) of members (a lead wire 31, a lead wire covering layer 32, a shield lead wire 33, and an external covering layer 34) housed at the later-described step S40.

<S10D: Electrode Film Arrangement Step>

Figure 6:
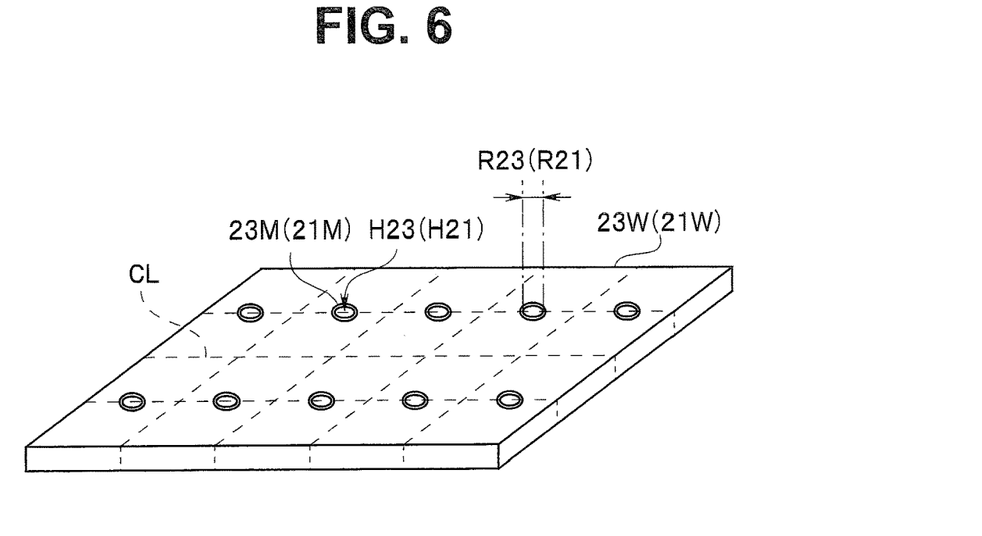
FIG. 6 is a perspective view of a semiconductor wafer according to the first embodiment.

As shown in FIG. 6, on wall surfaces of the through-holes H21 and H23 in the device wafers 21W and 23W, electrode films 21M and 23M are arranged via insulation layers (silicon oxide layers or the like), not shown, by employing, for example, a plating method.

The electrode film 23M formed of Cu, Au, SnAg, or Sn is connected to the planar device 28 or the like by rewiring.

In addition, not only on the wall surfaces of the through-hole H21, but also on front surfaces and rear surfaces of the device wafers 21W and 23W, ring-like electrode films connected to the electrode films 21M and 23M may be arranged so as to surround the through-holes H21 and H23.

On the other hand, for the through-holes of the device wafers 22W and 24W, insulation layers, not shown, are formed, whereas electrode films are not arranged.

<Step S20> Lamination Step

Figure 7:
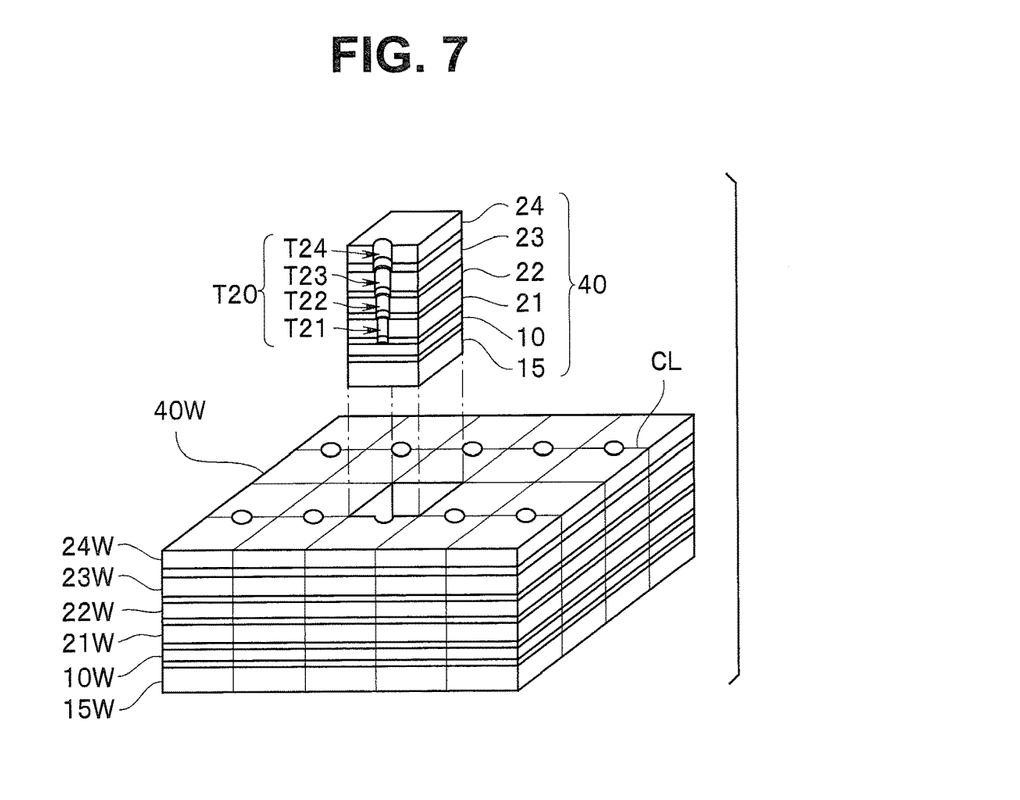
FIG. 7 is a perspective view of a laminated wafer according to the first embodiment.

As shown in FIG. 7, the glass wafer 15W, the image pickup wafer 10W, and the device wafers 21W to 24W are laminated and thus, a laminated wafer 40W is fabricated. The image pickup wafer 10W and the device wafers 21W to 24W on which the image pickup devices 10 and semiconductor devices 21 to 24 having the same sizes are arranged in the same arrangement are positioned, the bumps 27 are bonded, and an uncured liquid resin is injected respectively between the wafers. The liquid resin is solidified by cure treatment and becomes resin layers. Positioning of the device wafers 21W to 24W is conducted, for example, such that the centers of the through-holes T21 to T24 are respectively matched.

The glass wafer 15W and the image pickup wafer 10W are bonded via a transparent bonding layer 19. Note that as described above, the glass wafer 15W and the image pickup wafer 10W may be bonded prior to the lamination step. Further, no glass wafer 15W may be laminated. In other words, in the image pickup unit 1, the cover glass 15 is not an essential component. In addition, on a front surface of the glass wafer 15W, a plurality of optical wafers respectively including a plurality of optical elements (for example, lenses, filters, or spacers) may be laminated.

In addition, prior to the lamination step, the bumps 27 may be bonded, the device wafers 21W to 24W may be bonded via the sealing resin layers 29, and thus, the device laminate wafer may be fabricated.

Here, when the device wafers 21W to 24W are bonded, it is likely that the liquid resin enters the through-holes H21 and H23 and covers surfaces of the electrode films 21M and 23M. Therefore, it is preferable that in the through-holes, portions (resin reservoirs) having diameters larger than diameters of central portions of the through-holes are formed on end portions of the through-holes, for example, by two-stepped processing.

<Step S30> Cutting Step

As shown in FIG. 7, the laminated wafer 40W is cut along cutting lines CL and is diced into a plurality of image pickup laminates 40. The cutting lines CL are designed to pass through the centers of the through-holes H21 to H24 of the laminated wafer 40W. Therefore, the through-holes H21 to H24 having circular sectional views become the cutouts T21 to T24 each being of the semicircular shape in the side surfaces of the image pickup laminate 40 by cutting. The electrode films 21M and 23M on the wall surfaces of the through-holes H21 and H23 of the laminated wafer 40W become the side electrodes 21C and 23C arranged in internal surfaces (cutout surfaces) of the cutouts T21 and T23.

<Step S40> Cable Bonding Step

A signal cable 30 which is an electric member having a size in accordance with a size of a groove T20 of the device laminate 20 is housed in and bonded to the groove T20. Sizes (diameters: widths and depths, lengths) of respective portions of the groove T20 are set so as to be, for example, 1% to 50% larger than sizes (diameters/bonding lengths) of respective portions of the signal cable 30.

For example, the diameter R21 of the cutout T21 and the diameter R31 of the lead wire 31 are in relationship of (R21≥R31) and preferably, are in relationship of (1.01× R31<R21<1.20×R31). In addition, the diameter R22 of the cutout T22 and the diameter R32 of the lead wire covering layer 32 are in relationship of (R22≥R32) and preferably, are in relationship of (1.01×R32<R22<1.50×R32).

A length of each of the lead wire 31, the lead wire covering layer 32, and the shield lead wire 33 is set to be substantially the same as a thickness of each of the semiconductor devices 21 to 23 (and of the sealing resin layers 29).

The two electrode parts (the lead wire 31 and the shield lead wire 33) of the signal cable 30 are bonded to the side electrodes 21C and 23C via a conductive paste (solder, Ag) and thus, the image pickup unit 1 is completed.

According to the method for manufacturing the present embodiment, a short and small image pickup unit 1 can be easily manufactured. In other words, for example, the step of forming the through-hole H23 having the predetermined diameter R23 in the device wafer 23W and the step of arranging the electrode film 23M in the wall surface of the through-hole 1123 are steps in the heretofore known easy method. Through cutting the laminated wafer 40W, a plurality of image pickup laminates 40, in each of which the side electrodes 21C and 23C are arranged in the groove T20 constituted of the plurality of cutouts T21 to T24, can be simultaneously and collectively fabricated.

Note that the laminated semiconductor devices are insulated by the sealing resin layers. Therefore, although the plurality of semiconductor devices (a first device and a second device) in which the side electrodes are arranged are essential components, the semiconductor device (a third device) in which no side electrode is arranged is not an essential component. In other words, it is not required that the side electrodes are arranged in the cutout surfaces of all of the semiconductor devices, and it is only required that side electrodes of at least one of the semiconductor devices be arranged.

In other words, in the device wafer fabrication step, the image pickup wafer including the plurality of image pickup devices, the first device wafer including a plurality of first semiconductor devices, and the second device wafer including a plurality of second semiconductor devices are at least fabricated. In the through-hole formation step, a plurality of first through-holes are formed in the predetermined arrangement in the first device wafer and a plurality of second through-holes are formed in the predetermined arrangement in the second device wafer. In the electrode film arrangement step, first electrode films are arranged on respective wall surfaces of the plurality of first through-holes of the first device wafer, and second electrode films are arranged on respective wall surfaces of the plurality of second through-holes of the second device wafer. In the lamination step, the image pickup wafer, the first device wafer, and the second device wafer are laminated via the sealing resin layers so as to superimpose the first through-holes and the second through-holes and thus, the laminated wafer is fabricated. In the cutting step, the laminated wafer is cut along the cutting lines each passing through the centers of the first through-holes, the device laminate including the groove in the side surfaces, in which the first electrode film and the second electrode film are arranged in the internal surfaces, is fabricated. In the bonding step, the electric members having the sizes in accordance with the sizes of the groove are housed in the groove, and the two electrodes of the electric members are bonded to the first electrode film or the second electrode film.

Note that it is preferable that a third device wafer including a plurality of third through-holes, on which no electrode films are arranged on wall surfaces of the third through-holes, is laminated between the first device wafer and the second device wafer.

In addition, when the electric member includes three or more electrode parts, in order to cope with the three or more electrode parts, a device laminate in which semiconductor devices including three or more side electrodes are laminated is fabricated.

<Modification of First Embodiment>

Since image pickup units 1A to 1D of modifications of a first embodiment are similar to an image pickup unit 1 and have the same effects as those of the image pickup unit 1, components having the same functions as those of the image pickup unit 1 are denoted by the same reference numerals and symbols, and the description for those will be omitted.

<Modification 1 of First Embodiment>

Figure 8A:
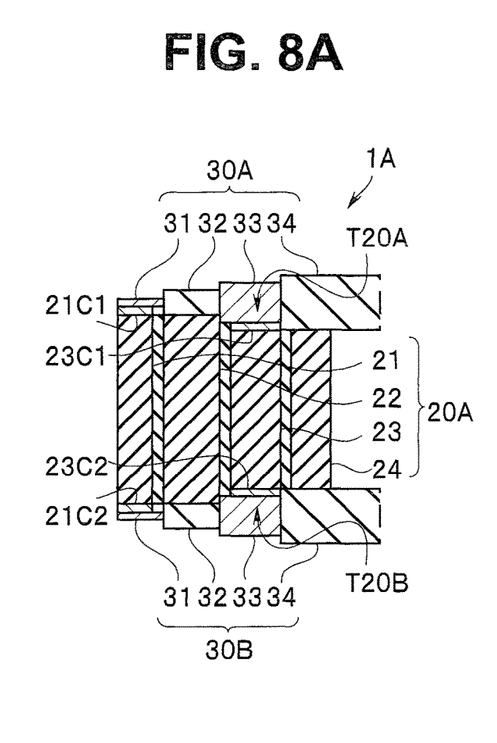
FIG. 8A is a sectional view of an image pickup unit of a modification 1 according to the first embodiment.

As shown in FIG. 8A, an image pickup unit 1A of a modification 1 includes two signal cables 30A and 30B. A device laminate 20A of the image pickup unit 1A is configured to include grooves T20A and T20B on upper and lower side surfaces of the device laminate 20A, which face each other. A lead wire 31 and a shield lead wire 33 of the signal cable 30A are bonded to side electrodes 21C1 and 23C1, respectively and a lead wire 31 and a shield lead wire 33 of the signal cable 30B are bonded to side electrodes 21C2 and 23C2, respectively. The side electrodes 21C1 and 21C2 are insulated from each other, and the side electrodes 23C1 and 23C2 are insulated from each other.

In other words, the image pickup unit 1A is configured to include the grooves T20A and T2OB on the two upper and lower side surfaces of the device laminate 20A, which face each other, and the signal cables 30A and 30B are housed in and bonded to the plurality of grooves T20A and T20B, respectively.

Note that although the image pickup unit 1A is configured to include the grooves T20A and T2OB formed on the two side surfaces of the device laminate 20A, grooves may be formed on two side surfaces which are orthogonal to each other or on three or more side surfaces. Further, a plurality of grooves may be formed on one side surface. In each of the grooves, electric members having configurations which are different from one another may be housed.

<Modification 2 of First Embodiment>

Figure 8B:
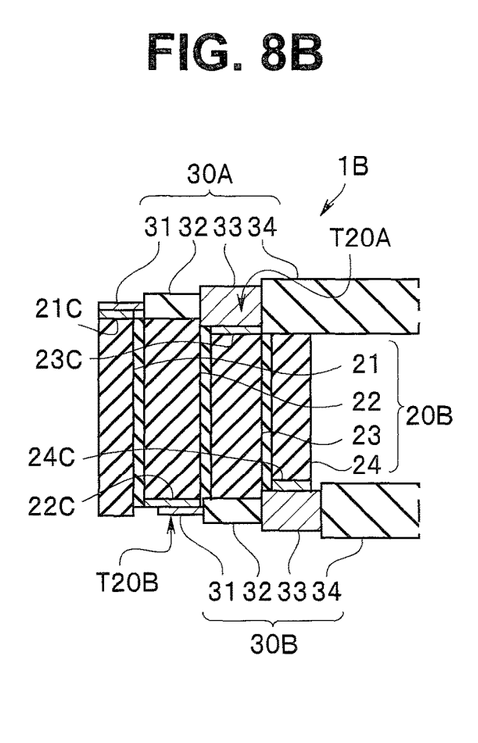
FIG. 8B is a sectional view of an image pickup unit of a modification 2 according to the first embodiment.

As shown in FIG. 8B, an image pickup unit 1B of a modification 2 is configured such that a lead wire 31 of a signal cable 30A is connected to a side electrode 21C of a semiconductor device 21 and a shield lead wire 33 of the signal cable 30A is connected to a side electrode 23C of a semiconductor device 23, respectively. On the other hand, a lead wire 31 of a signal cable 30B is connected to a side electrode 22C of a semiconductor device 22 and a shield lead wire 33 of the signal cable 30B is connected to a side electrode 24C of a semiconductor device 24, respectively.

In other words, the image pickup unit 1B is configured to include the signal cables 30A and 30B which are housed in the two side surfaces of a device laminate 20B, respectively. The signal cables 30A and 30B are respectively bonded to the side electrodes 21C to 24C of the semiconductor devices 21 to 24, each of which is different.

<Modifications 3 and 4 of First Embodiment>

Each of the image pickup units of the above-described embodiment and modifications is configured such that cutouts are formed in outer peripheral portions of all of a plurality of semiconductor devices.

Figure 9:
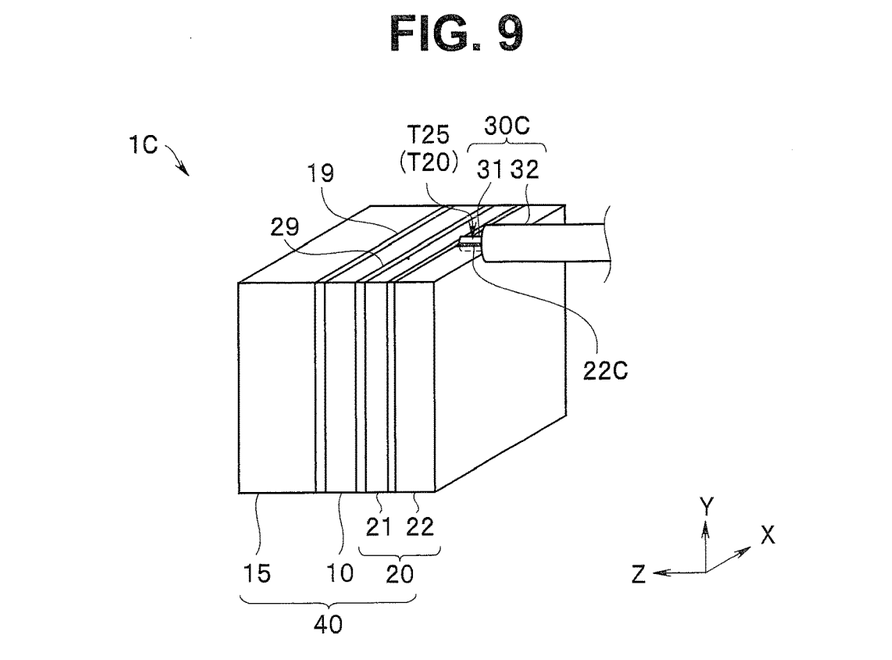
FIG. 9 is a perspective view of an image pickup unit of a modification 3 according to the first embodiment.

In contrast to this, as shown in FIG. 9, an image pickup unit 1C of a modification 3 is configured such that a cutout T25 is formed only in an outer peripheral portion of a semiconductor device 22 of laminated semiconductor devices 21 and 22, which is on a rearmost side (position farthest from the image pickup device 10). In other words, a groove T20 is configured by the cutout T25.

A signal cable 30C of the image pickup unit 1C is a simple line which is constituted of a core wire 31 and a lead wire covering layer 32 covering circumference of the core wire 31. The core wire 31 is bonded to a cutout surface, that is, a side electrode 22C which is arranged on an internal surface of the groove T20.

As described above, the image pickup unit 1C includes: an image pickup device having a light receiving surface and a rear surface facing the light receiving surface; a device laminate bonded on the rear surface of the image pickup device, in which a plurality of semiconductor devices are laminated via sealing resin layers; and an electric member including an electrode part. The cutout is formed in the outer peripheral portion of the semiconductor device of the plurality of semiconductor devices, which is laminated on the rearmost side. On the cutout surface, the side electrode is arranged. The electric member is housed in the cutout. The electrode part of the electric member is bonded to the side electrode.

Further, in the image pickup unit 1C, the electric member is the simple line which includes the lead wire and the external covering layer covering the lead wire, and the lead wire is bonded to the side electrode.

Figure 10:
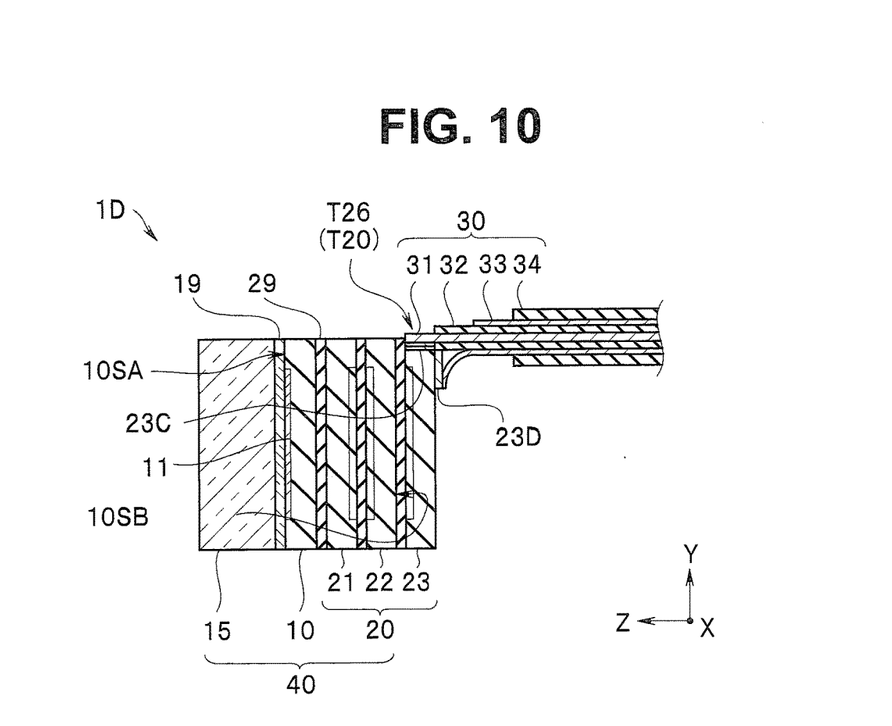
FIG. 10 is a sectional view of the image pickup unit of the modification 3 according to the first embodiment.

In addition, in an image pickup unit 1D of a modification 43 shown in FIG. 10, a cutout T26 is formed only in an outer peripheral portion of a semiconductor device 23 among laminated semiconductor devices 21, 22, and 23, which is arranged on a rearmost side. In other words, a groove T20 is configured by the cutout T26.

A core wire 31 of a signal cable 30C is bonded to a cutout surface, that is, a side electrode 23C arranged on an internal surface of the groove T20. On the other hand, a shield lead wire 33 is bonded to an electrode 23D arranged on a rear surface of the semiconductor device 23. Note that no connection may be arranged between the shield lead wire 33 and the image pickup unit.

In addition, the image pickup unit may be configured such that cutouts are formed in outer peripheral portions of the plurality of successively laminated semiconductor devices among the plurality of semiconductor devices of a device laminate, which include the semiconductor device laminated on the rearmost side; a groove in parallel with an optical axis direction is configured on a side surface of the device laminate by the plurality of cutouts which communicate with one another; a side electrode is arranged on at least one of cutout surfaces; an electric member is housed in the groove; and the electrode part of the electric member is bonded to the side electrode.

In addition, the device laminate 20 bonded onto a rear surface 10SB of an image pickup device 10 may be configured by only one semiconductor device, for example, the semiconductor device 23.

Second Embodiment

Since an image pickup unit 1E of a second embodiment is similar to an image pickup unit 1 and the like and has the same effects as those of the image pickup unit 1 and the like, components having the same functions as those of the image pickup unit 1 and the like are denoted by the same reference numerals and symbols, and the description for those will be omitted.

Figure 11A:
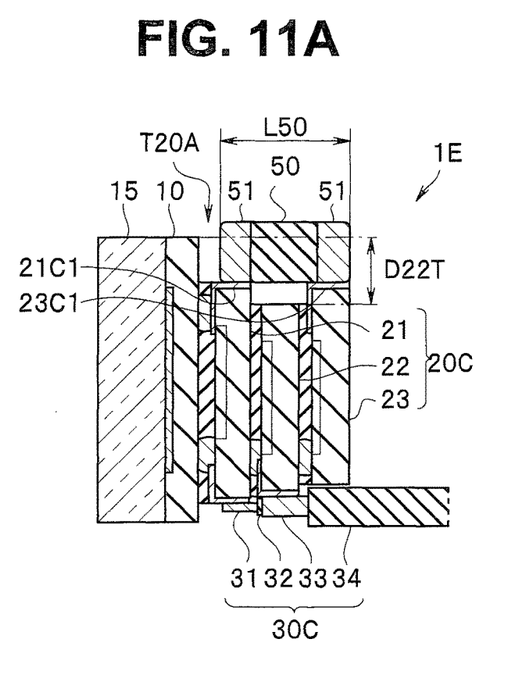
FIG. 11A is a sectional view of an image pickup unit according to a second embodiment.
Figure 11B:
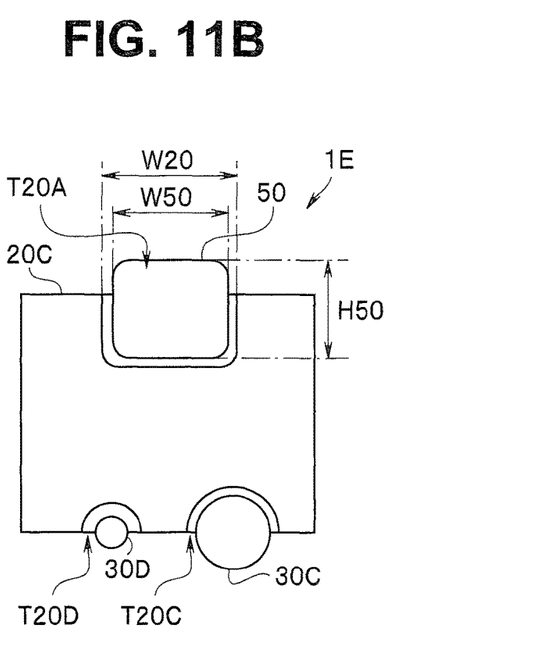
FIG. 11B is a schematic view of a back surface of the image pickup unit according to the second embodiment.

In the image pickup unit 1E, a plurality of electric members (a chip capacitor 50 and two signal cables 30C and 30D) having configurations which are different from one another are housed in and bonded to respective grooves of upper and lower side surfaces of a device laminate.

In other words, as shown in FIG. 11A and FIG. 11B, in the image pickup unit 1E, the chip capacitor 50 and the two signal cables 30C and 30D are housed in grooves T20A, T20C, and T20D in sizes according to respective sizes of the chip capacitor 50 and the two signal cables 30C and 30D, respectively and are bonded to respective side electrodes.

A device laminate 20C includes the three grooves T20A, T20C, and T20D. In order to house the chip capacitor 50, a size of the groove T20A is designed in accordance with a size (a length L of 50, a width W of 50, and a height H of 50) of the chip capacitor 50, and a shape of the groove T20A in a sectional view is substantially rectangular.

Two electrodes 51 of the chip capacitor 50 are bonded to side electrodes 21C1 and 23C1 arranged on internal surfaces of the groove T20A of the device laminate 20C, respectively. In other words, in accordance with a length between the electrodes 51 of the chip capacitor 50, thicknesses of a semiconductor device 22 and a sealing resin are set.

The groove T20A which is substantially rectangular in the sectional view is prepared by forming through-holes, which have the same sizes as one another and are substantially rectangular, in three device wafers and by conducting cutting. In other words, sizes of a plurality of semiconductor devices 21 to 23, on which the groove T20A is formed in which an electronic component including a plurality of constituent members in sizes differing from one another is not housed, may be the same.

As shown in FIG. 11B, a width W20 of a cutout of the semiconductor device 22 in the groove T20A is set in accordance with a width W50 of the chip capacitor 50 and is the same as a width of a cutout of each of semiconductor devices 21 and 23.

Note that as shown in FIG. 11A, in the image pickup unit 1E, a depth D22T of the cutout of the semiconductor device 22 in the groove T20A is larger than a depth of the cutout of each of the semiconductor devices 21 and 23 and sizes of the depth D22T of the cutout of the semiconductor device 22 in the groove T20A and the depth of the cutout of each of the semiconductor devices 21 and 23 are different from each other. This is because upon laminating the semiconductor devices 21, 22, and 23, the side electrodes 21C1 and 23C1 are designed so as not to be covered by sealing resins.

In addition, although a side surface of the chip capacitor 50 protrudes from an upper surface of the device laminate 20C, the depth of the groove T20A may be made deep and the chip capacitor 50 may be completely housed inside the groove T20A.

Note that since a diameter of the signal cable 30D is smaller than a diameter of the signal cable 30C, the groove T20D is smaller than the groove T20C.

The chip component housed in the groove of the image pickup unit 1E may be a chip inductor, a noise filter, or the like.

As described above, the plurality of grooves may be configured on the plurality of side surfaces of the device laminate, and respective electric members may be housed in the plurality of grooves.

Third Embodiment

Since an image pickup unit 1F of a third embodiment is similar to an image pickup unit 1 and the like and has the same effects as those of the image pickup unit 1 and the like, components having the same functions as those of the image pickup unit 1 and the like are denoted by the same reference numerals and symbols, and the description for those will be omitted.

Figure 12A:
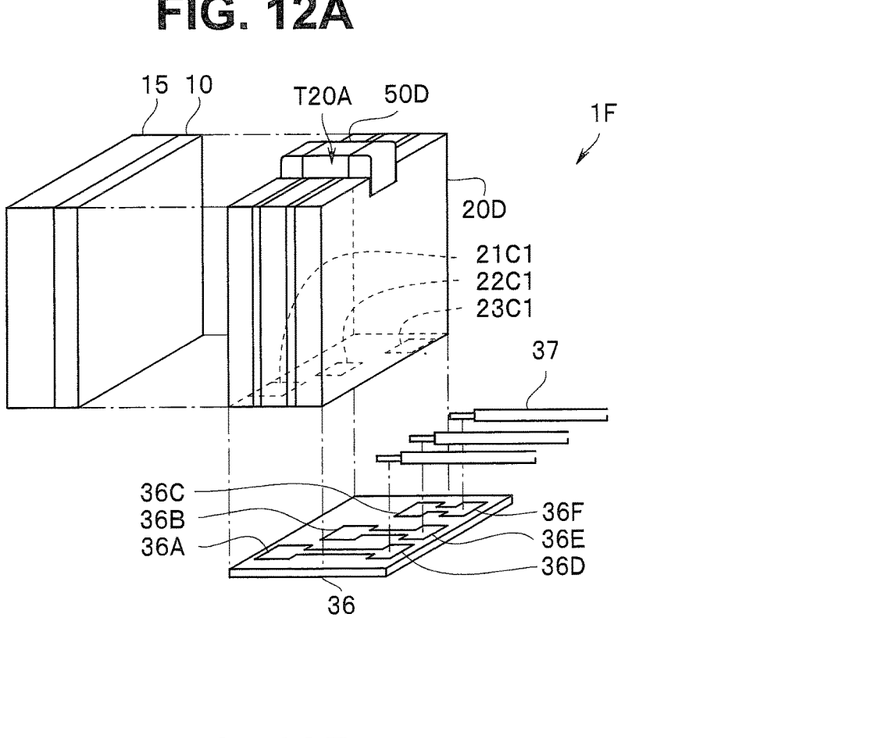
FIG. 12A is an exploded view of an image pickup unit according to a third embodiment.
Figure 12B:
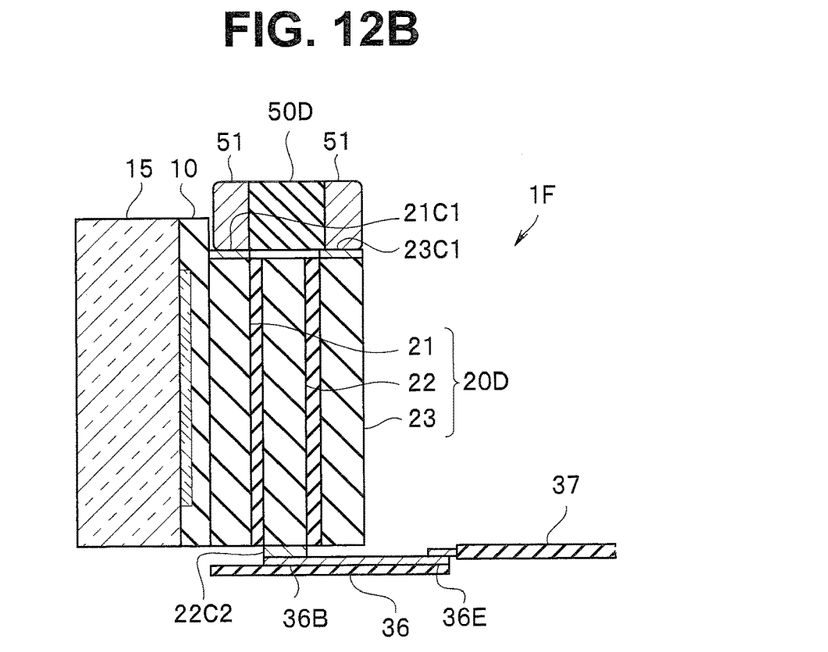
FIG. 12B is a sectional view of the image pickup unit according to the third embodiment.

As shown in FIG. 12A and FIG. 12B, an image pickup unit 1F includes three signal cables 37A to 37C and a wiring board 36. The wiring board 36 includes first electrodes 36A to 36C in a distal end portion and second electrodes 36D to 36F in a rear end portion, which are connected to the first electrodes 36A to 36C.

Note that in a device laminate 20D, in a groove T20A on a side surface, a chip inductor 50D is housed and two electrodes 51 of the chip inductor 50D are bonded to side electrodes 21C1 and 23C1 arranged on internal surfaces of the groove T20A of the device laminate 20D.

Further, the device laminate 20D includes second side electrodes 21C2, 22C2, and 23C2 on a lower surface of the device laminate 20D. In other words, unlike the side electrodes 21C1 and 23C1, the second side electrodes 21C2, 22C2, and 23C2 are not arranged inside a groove.

The second side electrodes 21C2, 22C2, and 23C2 are bonded to the first electrodes 36A to 36C of the wiring board 36. Signal cables 37A to 37C are bonded to the second electrodes 36D to 36F of the wiring board 36.

In other words, when many signal cables are connected, in order to ensure a bonding area, the wiring board is bonded to the device laminate, and the plurality of signal cables are bonded to the wiring board.

Here, in the conventional method in which the wiring board is bonded onto a rearmost surface of the device laminate, in order to bond the signal cable or signal cables, it is required to bend the wiring board at a substantially right angle. In contrast to this, in the image pickup unit 1F, the wiring board which is a flat plate is used as it is. Therefore, not only the plurality of signal cables 37A to 37C can be easily housed, but also reliability of bonding the device laminate 20D and the wiring board 36 is enhanced.

Modification of Third Embodiment

Since an image pickup unit 1G of a modification of a third embodiment is similar to an image pickup unit 1F and the like and has the same effects as those of the image pickup unit 1F and the like, components having the same functions as those of the image pickup unit 1F and the like are denoted by the same reference numerals and symbols, and the description for those will be omitted.

In the above-described embodiments and modifications, the external dimension (a height or a width) in the direction orthogonal to the optical axis of the device laminate 20D is the same as the size of the image pickup device 10 in the plan view, the device laminate 20D projected in the projection plane in the direction orthogonal to the optical axis is arranged within the projection plane of the image pickup device 10. However, distal end portions of the component and the signal cables mounted on the side surfaces of the device laminate 20D are not housed within the projection plane of the image pickup device 10.

Figure 13:
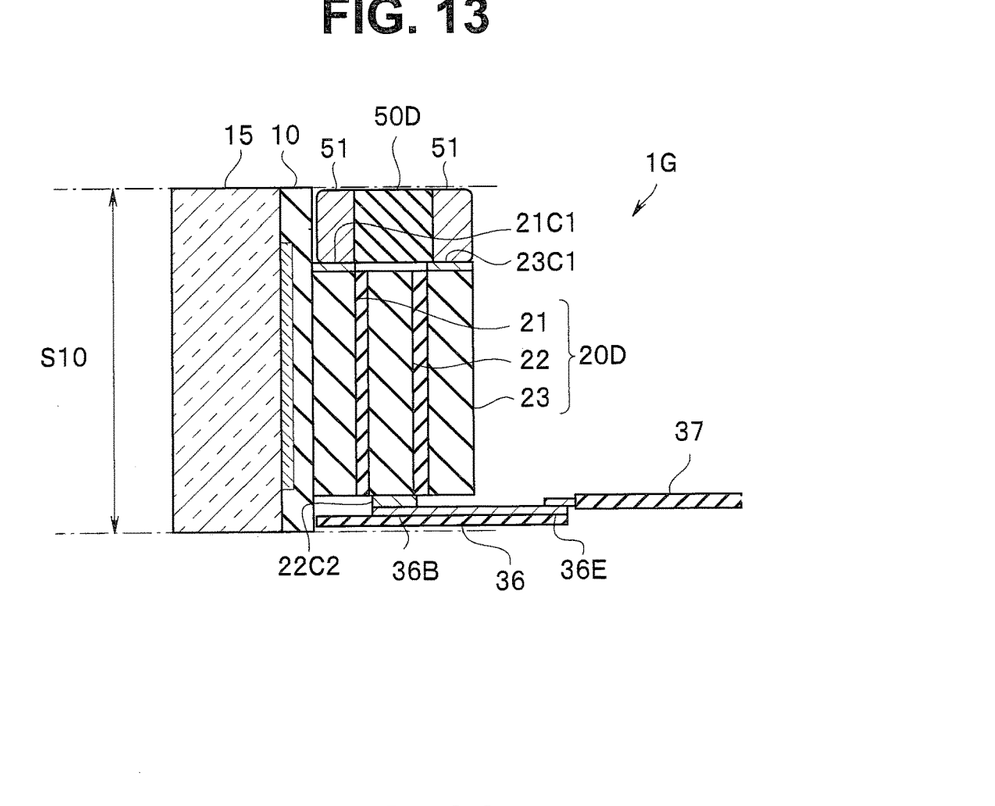
FIG. 13 is a perspective view of an image pickup unit of a modification according to the third embodiment.

In contrast to this, as shown in FIG. 13, in the image pickup unit 1G of the modification of the third embodiment, components of the image pickup unit 1F including distal end portions of an electronic component 50D, a wiring board 36, and a signal cable 37, which are mounted on side surfaces of a device laminate 20D, are arranged within a projection plane (S10) of an image pickup device 10.

A diameter of the image pickup unit 1G is further smaller than a diameter of the image pickup unit 1 and the like.

Note that it is needless to say that when the components of the image pickup unit are arranged within the projection plane (S10) of the image pickup device 10, each of the image pickup units 1 to 1G has the same effects as those of the image pickup unit 1G.

Fourth Embodiment

An endoscope of a fourth embodiment includes any of the above-described image pickup units 1 and 1A to 1G.

Figure 14:
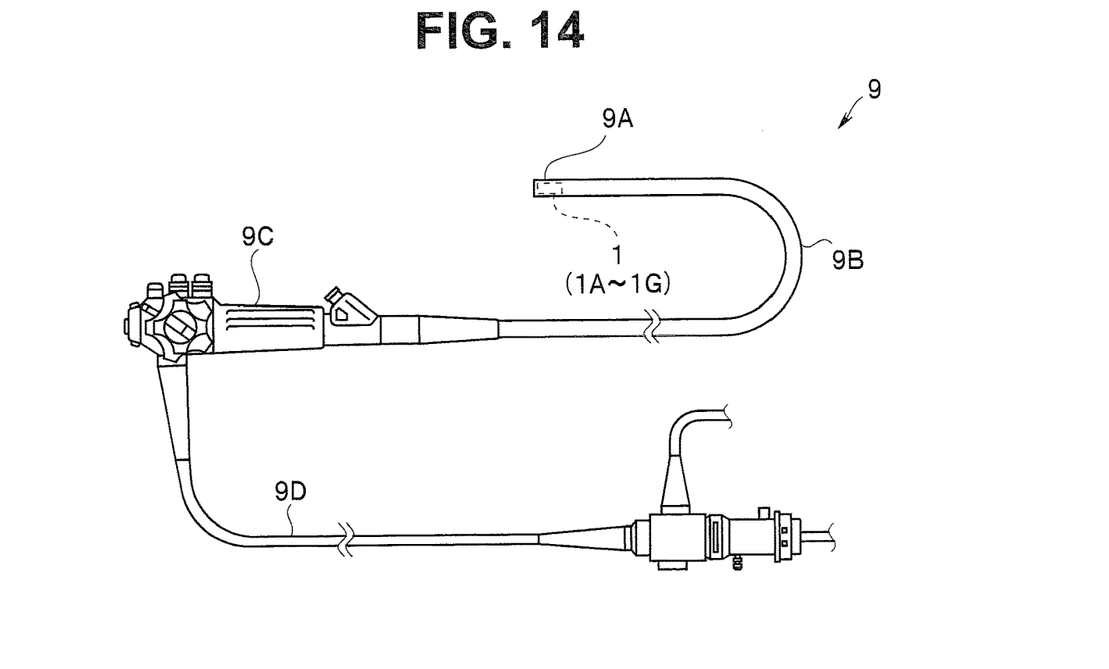
FIG. 14 is a perspective view of an endoscope according to a fourth embodiment.

As shown in FIG. 14, an endoscope 9 includes an insertion portion 9B having a distal end portion 9A in which an image pickup unit 1 being small-sized and easily manufactured is housed; an operation portion 9C arranged on a proximal end side of the insertion portion 9B; and a universal cord 9D extending from the operation portion 9C. The universal cord 9D is connected to a signal cable 30 of the image pickup unit.

Because the endoscope 9 includes any of the short and small image pickup units 1 and 1A to 1G in the distal end portion 9A of the insertion portion 9B, the endoscope 9 is minimally invasive, and manufacturing the endoscope 9 is easy. Note that although the endoscope 9 is a flexible endoscope, the endoscope 9 may be a rigid endoscope. In addition, the endoscope of the embodiment may be a capsule type endoscope including any of the image pickup units 1 and 1A to 1G and may be a medical endoscope or an industrial endoscope.

The present invention is not limited to the above-described embodiments and modifications, and a variety of modifications and variations are possible in the scope of not changing the gist of the present invention.

What is claimed is:

1. A method for manufacturing an image pickup unit comprising:
    fabricating an image pickup semiconductor wafer comprising a plurality of image pickup sensors, the image pickup semiconductor wafer having a light receiving surface and a rear surface opposite to the light receiving surface;
    fabricating a first semiconductor wafer comprising a plurality of first semiconductor devices;
    fabricating a second semiconductor wafer comprising a plurality of second semiconductor devices;
    forming a plurality of first through-holes in a predetermined arrangement in the first semiconductor wafer;
    forming a plurality of second through-holes in the predetermined arrangement in the second semiconductor wafer;
    arranging a first electrode film on a wall surface of each of the plurality of first through-holes of the first semiconductor wafer;
    arranging a second electrode film on a wall surface of each of the plurality of second through-holes of the second semiconductor wafer;
    fabricating a laminated wafer by laminating the image pickup semiconductor wafer, the first semiconductor wafer, and the second semiconductor wafer via sealing resin layers such that the first through-holes and the second through-holes have a common center axis and the first and second electrode films are electrically insulated from each other;
    cutting the laminated wafer along cutting lines passing through the common center axis to fabricate a device laminate having a groove on a side surface of the device laminate such that each of the first electrode film and the second electrode film being arranged on an internal surface of the groove;
    housing an electric member having first and second electrodes in the groove, the first and second electrodes being electrically insulated from each other and each of the first and second electrodes having a size in accordance with a respective size of the groove; and
    bonding the first electrode and the second electrode of the electric member to the first electrode film and to the second electrode film, respectively.

2. The method for manufacturing the image pickup unit according to claim 1, further comprising:
    fabricating a third semiconductor wafer; and forming a plurality of third through-holes in the predetermined arrangement in the third semiconductor wafer, for each of the plurality of third through-holes an electrode film is not arranged on a wall surface;
wherein the laminating comprising laminating the third semiconductor wafer between the first semiconductor wafer and the second semiconductor wafer.

3. The method for manufacturing the image pickup unit according to claim 1, wherein
the electric member includes a plurality of constituent members in sizes differing from one another, and
the groove of the device laminate includes a plurality of grooves in sizes differing from one another and are in accordance with the sizes of the housed constituent members.

4. The method for manufacturing the image pickup unit according to claim 1, wherein
the electric member is a shielded cable including a lead wire, a lead wire covering layer covering the lead wire, a shield lead wire covering the lead wire covering layer, and an external covering layer covering the shield lead wire, the lead wire comprises the first electrode and the shield lead wire comprises the second electrode,
the lead wire is housed in a portion of the groove corresponding to the first through-hole and is bonded to the first electrode film, and
the shield lead wire is housed in a portion of the groove corresponding to the second through-hole and is bonded to the second electrode film side.

5. The method for manufacturing the image pickup unit according to claim 2, wherein
the electric member is a shielded cable including a lead wire, a lead wire covering layer covering the lead wire, a shield lead wire covering the lead wire covering layer, and an external covering layer covering the shield lead wire, the lead wire comprises the first electrode and the shield lead wire comprises the second electrode,
the lead wire is housed in a portion of the groove corresponding to the first through-hole and is bonded to the first electrode film,
the lead wire covering layer is housed in a portion of the groove corresponding to the third through-hole, and
the shield lead wire is housed in a portion of the groove corresponding to the second through-hole and is bonded to the second electrode film.

6. The method for manufacturing the image pickup unit according to claim 2, further comprising:
fabricating a fourth semiconductor wafer; and
forming a plurality of fourth through-holes in the predetermined arrangement in the fourth semiconductor wafer, for each of the plurality of fourth through-holes the electrode film is not arranged on a wall surface;
wherein the laminating comprising laminating the third semiconductor device on a first side of the second semiconductor device and laminating the fourth semiconductor wafer on a second side of the second semiconductor wafer.

7. The method for manufacturing the image pickup unit according to claim 6, wherein
the electric member is a shielded cable including a lead wire, a lead wire covering layer covering the lead wire, a shield lead wire covering the lead wire covering layer, and an external covering layer covering the shield lead wire, the lead wire comprises the first electrode and the shield lead wire comprises the second electrode,
the lead wire is housed in a portion of the groove corresponding to the first through-hole and is bonded to the first electrode film,
the lead wire covering layer is housed in a portion of the groove corresponding to the third through-hole,
the shield lead wire is housed in a portion of the groove corresponding to the second through-hole and is bonded to the second electrode film; and
the external covering layer is housed in a portion of the groove corresponding to the fourth through-hole.

* * * * *